US012207888B2

(12) United States Patent
Schneider et al.

(10) Patent No.: US 12,207,888 B2
(45) Date of Patent: Jan. 28, 2025

(54) MAGNETIC TRACKING CALIBRATION VIA DISTORTION CORRECTION FOR ELECTROMAGNETIC FIELDS USING INSIDE-OUT TRACKING

(71) Applicant: Northern Digital Inc., Waterloo (CA)

(72) Inventors: Mark Robert Schneider, Williston, VT (US); Alec Duling, Milton, VT (US); Syamprasad Karyattuparambil Rajagopalan, Burlington, VT (US)

(73) Assignee: Northern Digital Inc., Waterloo (CA)

( * ) Notice: Subject to any disclaimer, the term of this patent is extended or adjusted under 35 U.S.C. 154(b) by 227 days.

(21) Appl. No.: 17/345,392

(22) Filed: Jun. 11, 2021

(65) Prior Publication Data
US 2021/0386485 A1 Dec. 16, 2021

Related U.S. Application Data

(60) Provisional application No. 63/038,702, filed on Jun. 12, 2020.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 90/39* (2016.02); *G01D 5/12* (2013.01);
(Continued)

(58) Field of Classification Search
CPC ............ A61B 34/20; A61B 2034/2055; A61B 2090/0811
See application file for complete search history.

(56) References Cited

U.S. PATENT DOCUMENTS 6,288,785 B1  9/2001 Frantz et al.
8,526,688 B2  9/2013 Groszmann et al.
(Continued)

FOREIGN PATENT DOCUMENTS

CN  1901835  1/2007
CN  1976638  6/2007
(Continued)

OTHER PUBLICATIONS

Borst, "Tracker calibration using tetrahedral mesh and tricubic spline models of warp," IEEE Virtual Reality 2004, Chicago, IL, USA, Mar. 27-31, 2004, pp. 19-26.
(Continued)

*Primary Examiner* — Serkan Akar
(74) *Attorney, Agent, or Firm* — Fish & Richardson P.C.

(57) ABSTRACT

A magnetic tracking device is configured to track an object in an environment by receiving a measurement of the non-magnetic signal and a corresponding measurement of the magnetic signal for a location of the magnetic tracking device in the environment. The magnetic tracking device estimates, based on the measurement of the non-magnetic signal, a non-magnetic pose of the magnetic tracking device in the environment for the location. The device estimates, based on the measurement of the magnetic signal, a magnetic pose of the magnetic tracking device in the environment for the location. The device determines a difference between the magnetic pose estimate and the non-magnetic pose estimate for the location. The device determines a magnetic distortion correction value for the location based on the difference. The magnetic tracking device generates a distortion correction model including the distortion value and outputs a representation of the distortion correction model.

9 Claims, 11 Drawing Sheets

(51) Int. Cl.
*A61B 90/00* (2016.01)
*G01D 5/12* (2006.01)

(52) U.S. Cl.
CPC .............. *A61B 2034/2051* (2016.02); *A61B 2034/2055* (2016.02); *A61B 2034/2061* (2016.02); *A61B 2034/2063* (2016.02); *A61B 2090/397* (2016.02)

(56) References Cited

U.S. PATENT DOCUMENTS

| | | | |
|---|---|---|---|
| 8,700,376 | B2 | 4/2014 | Ophir et al. |
| 9,165,114 | B2 | 10/2015 | Jain et al. |
| 9,733,336 | B2 | 8/2017 | Shen et al. |
| 10,064,687 | B2 | 9/2018 | Haimerl et al. |
| 10,095,815 | B2 | 10/2018 | Efrat et al. |
| 2005/0027192 | A1 | 2/2005 | Govari et al. |
| 2006/0258938 | A1 | 11/2006 | Hoffman et al. |
| 2009/0264740 | A1 | 10/2009 | Markowitz et al. |
| 2010/0168556 | A1 | 7/2010 | Shen et al. |
| 2019/0242952 | A1 | 2/2019 | Schneider et al. |
| 2020/0242339 | A1* | 7/2020 | Bustan .............. A61B 5/062 |
| 2020/0372409 | A1* | 11/2020 | Srivastava .......... G06N 3/08 |
| 2021/0096001 | A1 | 4/2021 | Schneider |

FOREIGN PATENT DOCUMENTS

| | | |
|---|---|---|
| CN | 102871662 | 1/2013 |
| CN | 105030331 | 11/2015 |
| CN | 105222772 | 1/2016 |
| CN | 103313675 | 2/2017 |
| CN | 107072740 | 8/2017 |
| CN | 210077846 | 2/2020 |
| CN | 109620408 | 6/2020 |
| EP | 3351201 | 7/2018 |

OTHER PUBLICATIONS

Bryson, "Measurement and calibration of static distortion of position data from 3D trackers," Proceedings of the SPIE, Jun. 1992, 1669;244-255.

Ikits et al., "An Improved Calibration Framework for Electromagnetic Tracking Devices," Proceedings IEEE Virtual Reality 2001, Mar. 13-17, 2001, 8 pages.

Kindratenko, "A survey of electromagnetic position tracker calibration techniques," Virtual Reality, Sep. 2000, 5;169-182.

Matinfar et al., "Absolute vs relative error characterization of electromagnetic tracking accuracy," Proceedings vol. 7625, Medical Imaging 2010: Visualization, Image-Guided Procedures, and Modeling, Feb. 23, 2010, 9 pages.

Much "Error Classification and Propagation for Electromagnetic Tracking," Technische Universität München Fakultät für Informatik, Jan. 14, 2008, 102 pages.

Raymond-Jean-Baptiste, "Méthode de correction des erreurs de mesure appliquée à un système Fastrak 3SPACE," École De Technologie Supérieure Université Du Québec, Nov. 11, 2009, 280 pages (Machine Translation).

Wu et al., "A Framework for Calibration of Electromagnetic Surgical Navigation Systems," Proceedings 2003 IEEE/RSJ International Conference on Intelligent Robots and Systems, Las Vegas, Nevada, Oct. 27-31, 2003, 547-552.

Zachmann, "Distortion correction of magnetic fields for position tracking," Proceedings Computer Graphics International, Jun. 23-27, 1997, pp. 213-220.

* cited by examiner

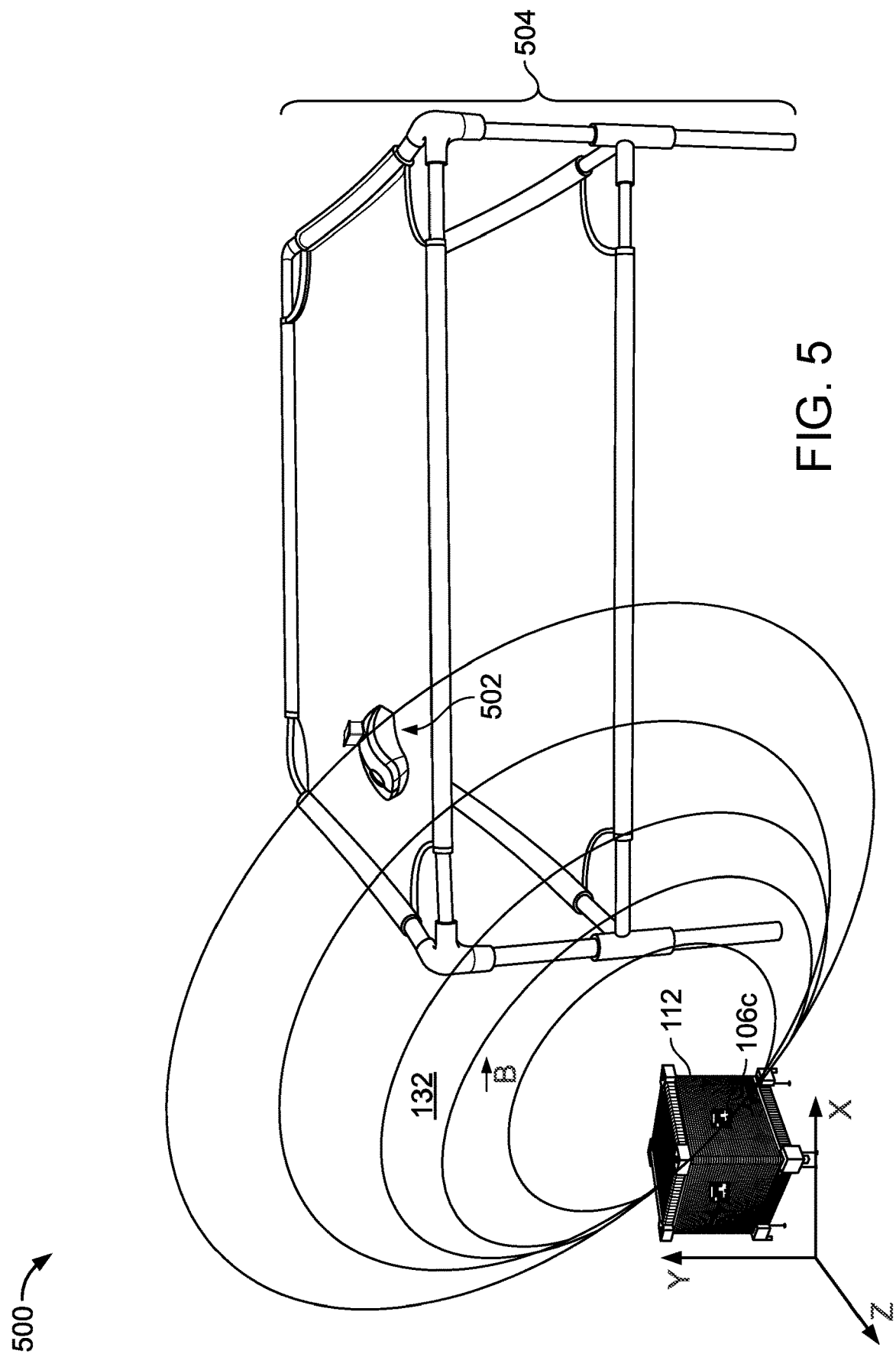

MAGNETIC TRACKING CALIBRATION VIA DISTORTION CORRECTION FOR ELECTROMAGNETIC FIELDS USING INSIDE-OUT TRACKING

CLAIM OF PRIORITY

This application claims priority under 35 U.S.C. § 119(e) to U.S. patent application Ser. No. 63/038,702, filed on Jun. 12, 2020, the entire contents of which are hereby incorporated by reference.

TECHNICAL FIELD

This disclosure relates to tracking one or more objects in a magnetic field, specifically a system for tracking a surgical instrument using electromagnetic (EM) signals.

BACKGROUND

Electromagnetic Tracking (EMT) systems are used to aid location of instruments and anatomy in medical procedures. Such systems can determine a position of a receiver based on measured field lines of a transmitted magnetic field.

SUMMARY

An Electromagnetic Tracking (EMT) system (also referred to as a magnetic tracking system) can be used to track a device for a number of applications, such as for medical applications during endoscope surgery or other types of surgery. The EMT system (also called a magnetic tracking system) includes at least one transmitter and at least one receiver. The transmitter emits, for example, a magnetic signal, and the receiver receives the magnetic signal and measures the magnetic signal. The measured magnetic signal provides information that the magnetic tracking system uses to determine relative locations of the transmitter with respect to the receiver (or vice versa). If the transmitter or receiver is affixed to another device (e.g., a tracked device), the magnetic tracking system can determine the relative location of the tracked device in the environment of the magnetic tracking system. In some implementations, the magnetic tracking system can detect distortions in the magnetic signal due to metallic objects in the environment. Numerous additional applications for tracking an object are known.

A magnetic tracking system described in this document includes a magnetic tracking device including a magnetic signal receiver and a non-magnetic signal receiver. The non-magnetic tracking device can include a visual tracking device, such as a camera. The non-magnetic tracking device is configured to measure additional data, in addition to the magnetic signal measured by the magnetic tracking device. The magnetic tracking system is configured to use the additional data (such as visual data) to determine how the magnetic signal is distorted in an environment of the magnetic tracking system. More specifically, the magnetic tracking system is configured to map these distortions to locations in the environment using the additional data at those locations as a ground truth signal.

Generally, the magnetic tracking system is configured to determine a location of one or more tracked objects with respect to a transmitter assembly, such as by detecting the magnetic signal emitted by the transmitter assembly. Often, objects in the environment of the magnetic tracking system cause the magnetic field emitted by the transmitter to be distorted in one or more regions of the environment. These distortions can cause errors in estimation of the position of a tracked object. It is useful to determine what these distortions are at as many locations as possible in the environment of the magnetic tracking system and compensate for the distortions during tracking of the tracked object.

To determine the distortions, the magnetic tracking system performs a calibration process. The magnetic tracking system maps a magnetic signal, measured by a receiver, at various locations in the environment and compares the measured magnetic signal to an expected, undistorted signal for those locations. The exact locations at which the magnetic signal is measured are determined by one or more non-magnetic techniques, such as by a visual techniques, ultrasonic signals, a radio signal, etc. Once the locations at which the receiver measured the magnetic signal are known, the magnetic tracking system can determine the distortions of the magnetic signal for each location.

Generally, the magnetic tracking system can use visual icons placed around the environment to determine the location of the receiver at various locations. In some implementations, the transmitter can be coupled to the camera and the receiver location is fixed. The visual icons can be placed at known locations in the environment, and a camera that is coupled to the magnetic receiver is configured to view the icons as the receiver is moved around the environment. The visual tracking system provides a location estimate for the receiver. The magnetic tracking system determines a difference between the measured magnetic signal at the estimated location and an expected magnetic signal at the location, as if the magnetic signal of the transmitter were undistorted. This undistorted, expected magnetic signal can be known for any location of the receiver in the environment. In some implementations, the expected magnetic signal can be determined based on receiving an input indicative of the location of the transmitter of the magnetic signal in the environment.

The techniques described herein include one or more of the following advantages. The magnetic tracking system is configured to more accurately determine what the position of the tracked device is by compensating for distortions in the magnetic signal. Placing visual markers around the environment of the magnetic tracking system for establishing a visual reference frame is a relatively low cost solution to compensate for magnetic distortions.

In a general aspect, a magnetic tracking system is configured for determining an object pose of a tracked object in an environment of the magnetic tracking system. The magnetic tracking system includes a non-magnetic signal detector configured to measure a non-magnetic signal in the environment. The magnetic tracking system includes a magnetic signal detector configured to measure a magnetic signal in the environment, the magnetic signal detector being coupled to the non-magnetic signal detector. The magnetic tracking system includes a computing device configured to perform the following operations. The computing device of the magnetic tracking system receives a measurement of the non-magnetic signal and a corresponding measurement of the magnetic signal for a location of the magnetic tracking device in the environment. The computing device estimates, based on the measurement of the non-magnetic signal, a non-magnetic pose of the magnetic tracking device in the environment for the location. The computing device estimates, based on the measurement of the magnetic signal, a magnetic pose of the magnetic tracking device in the environment for the location. The computing device determines a difference between the magnetic pose estimate and the non-magnetic pose estimate for the location. The computing device determines a magnetic distortion correction value for the location based on the difference. The computing device generates a distortion correction model including the distortion value. The computing device outputs a representation of the distortion correction model.

In some implementations, the non-magnetic signal is generated using a visual marker. In some implementations, the non-magnetic signal detector comprises a camera. In some implementations, the marker comprises an outer shape of the transmitter assembly, the outer shape being distinct from other outer shapes of other markers of a plurality of markers in the environment. In some implementations, the marker comprises an adhesive configured to removably affix the marker to another surface in the environment. In some implementations, the marker comprises an infrared retroreflector, and wherein the non-magnetic signal detector comprises an infrared source.

In some implementations, the non-magnetic signal comprises one of an ArUco pattern, a ChArUco pattern, a light source, an ultrasonic source, a radio signal source, or an outer shape of the transmitter assembly. In some implementations, the magnetic signal is generated by a transmitter assembly comprising: a memory configured to store calibration data related to the transmitter assembly, a processing device configured to control transmission of the magnetic signal from the transmitter assembly, a communication interface for sending and receiving data from the computing device, and a power source configured to provide electrical power to the memory, the processing device, and the communication interface.

In some implementations, the magnetic tracking system is configured for tracking a tracked object by performing operations comprising receiving a measurement of the magnetic signal at a particular location in the environment, retrieving the distortion correction model from a memory in communication with the computing device, determining a particular pose estimate for the tracked object, correcting the particular pose estimate based on a value of the distortion correction model corresponding to the particular location, and outputting a representation of the corrected particular pose estimate.

In some implementations, the tracked object comprises one of a catheter, an endoscope, or a surgical instrument.

In some implementations, the magnetic tracking system is configured for receiving a plurality of measurements of the magnetic signal corresponding to a known planar surface of the environment, the planar surface being associated with a scaffold that is positioned at a known location in the environment, for each measurement of the plurality of measurements of the magnetic signal, retrieving a predetermined correction value associated with a location of the measurement in the environment, determining, a distortion correction value for each measurement, and including the distortion correction value for each measurement in the distortion correction model.

In a general aspect, a process for determining an object pose of a tracked object in an environment of a magnetic tracking system includes measuring, by a non-magnetic signal detector, a non-magnetic signal in the environment. The process includes measuring, by a magnetic signal detector, a magnetic signal in the environment, wherein the magnetic signal detector is coupled to the non-magnetic signal detector. The process includes receiving a measurement of the non-magnetic signal and a corresponding measurement of the magnetic signal for a location of the magnetic tracking device in the environment. The process includes estimating, based on the measurement of the non-magnetic signal, a non-magnetic pose of the magnetic tracking device in the environment for the location. The process includes estimating, based on the measurement of the magnetic signal, a magnetic pose of the magnetic tracking device in the environment for the location. The process includes determining a difference between the magnetic pose estimate and the non-magnetic pose estimate for the location. The process includes determining a magnetic distortion correction value for the location based on the difference. The process includes generating a distortion correction model including the distortion value. The process includes outputting a representation of the distortion correction, such as a distortion map.

In some implementations, the non-magnetic signal is generated using a visual marker. In some implementations, the non-magnetic signal detector comprises a camera. In some implementations, the marker comprises an outer shape of the transmitter assembly, the outer shape being distinct from other outer shapes of other markers of a plurality of markers in the environment. In some implementations, the marker comprises an adhesive configured to removably affix the marker to another surface in the environment. In some implementations, the marker comprises an infrared retroreflector, and wherein the non-magnetic signal detector comprises an infrared source.

In some implementations, the non-magnetic signal comprises one of an ArUco pattern, a ChArUco pattern, a light source, an ultrasonic source, a radio signal source, or an outer shape of the transmitter assembly. In some implementations, the magnetic signal is generated by a transmitter assembly comprising: a memory configured to store calibration data related to the transmitter assembly, a processing device configured to control transmission of the magnetic signal from the transmitter assembly, a communication interface for sending and receiving data from the computing device, and a power source configured to provide electrical power to the memory, the processing device, and the communication interface.

In some implementations, the magnetic tracking system is configured for tracking a tracked object by performing operations comprising receiving a measurement of the magnetic signal at a particular location in the environment, retrieving the distortion correction model from a memory in communication with the computing device (e.g., a calculation of the distortion compensation), determining a particular pose estimate for the tracked object, correcting the particular pose estimate based on a value of the distortion correction model corresponding to the particular location, and outputting a representation of the corrected particular pose estimate.

In some implementations, the tracked object comprises one of a catheter, an endoscope, or a surgical instrument.

In some implementations, the magnetic tracking system is configured for receiving a plurality of measurements of the magnetic signal corresponding to a known planar surface of the environment, the planar surface being associated with a scaffold that is positioned at a known location in the environment, for each measurement of the plurality of measurements of the magnetic signal, retrieving a predetermined correction value associated with a location of the measurement in the environment, determining, a distortion correction value for each measurement, and including the distortion correction value for each measurement in the distortion correction model.

The details of one or more embodiments of the subject matter described herein are set forth in the accompanying drawings and the description below. Other features, objects, and advantages of the subject matter will be apparent from the description and drawings, and from the claims.

DESCRIPTION OF DRAWINGS

FIGS. 4A, 4B, and 5 show example scaffolds for calibration of the magnetic tracking systems of FIGS. 1-3.

Like reference symbols in the various drawings indicate like elements.

DETAILED DESCRIPTION

An Electromagnetic Tracking (EMT) system (also called a magnetic tracking system) can be used in various environments, such as medical settings, to track an object (e.g., a tracked object). For example, in a surgical setting, the EMT system can be used to track medical equipment (e.g., a surgical tool) for one or more purposes (e.g., endoscopic surgery), thereby allowing the three-dimensional position (e.g., location) and the orientation of the object to be known to a medical professional (e.g., a surgeon) during a medical procedure. Generally, the magnetic tracking system is configured to track objects inside a body to assist the medical professional with an operation performed by the medical professional.

Figure 1A:
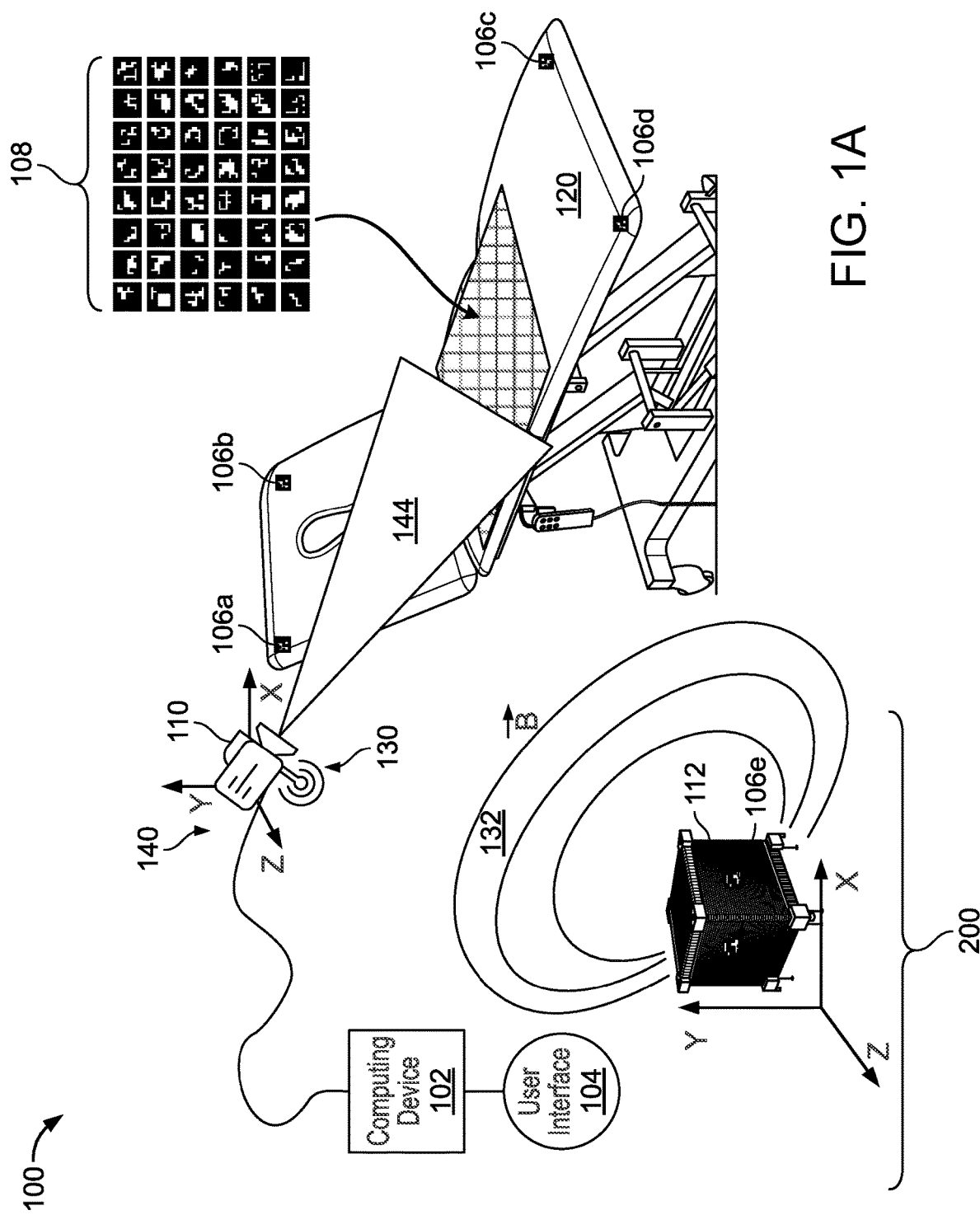
FIG. 1A shows a diagram of an environment including an example of a magnetic tracking system for calibrating the magnetic tracking system.
Figure 1B:
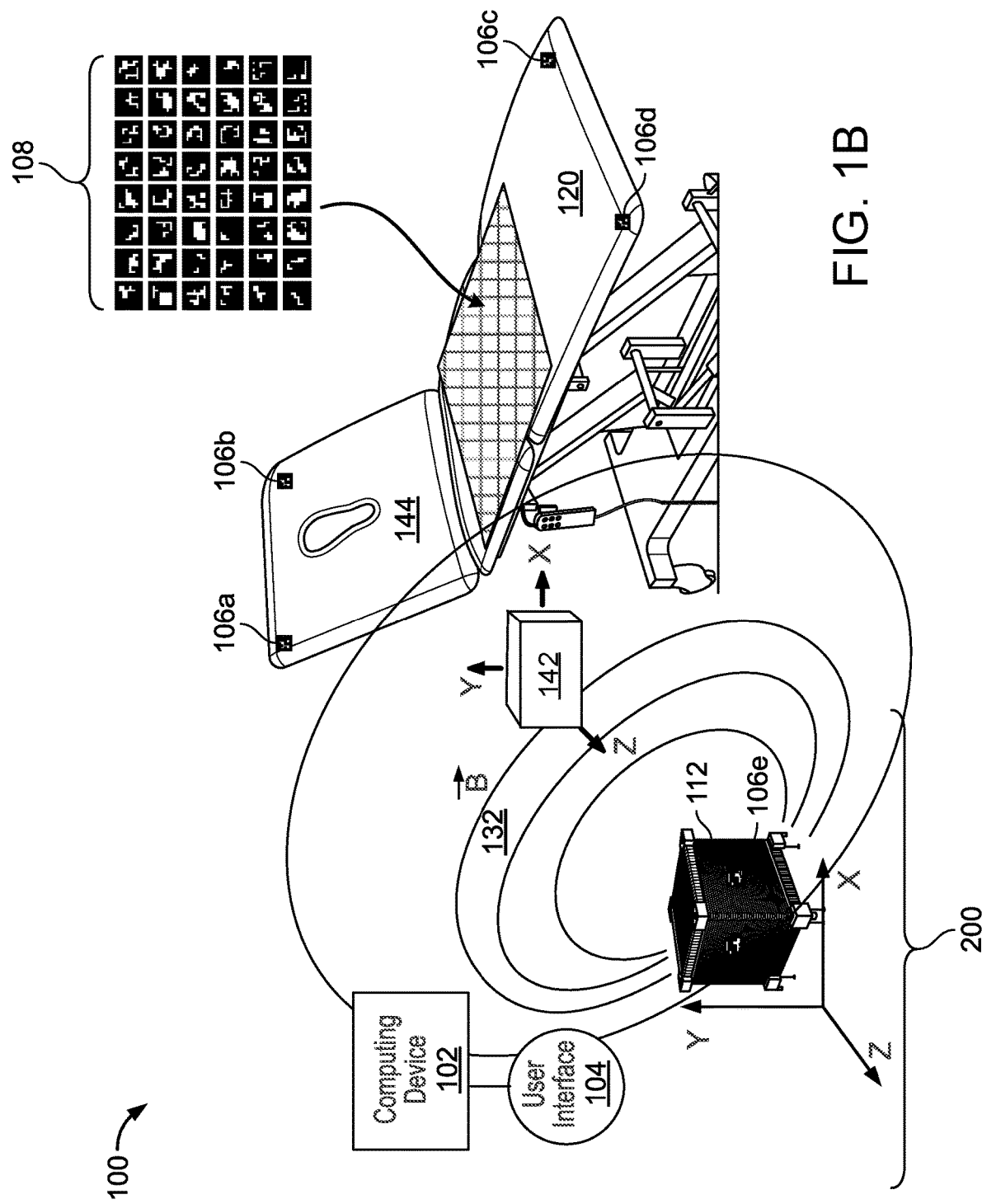
FIG. 1B shows a diagram of an environment including an example of a magnetic tracking system for tracking a tracked object.

FIG. 1A shows a diagram of an environment including an example of a magnetic tracking system 100 for calibrating the magnetic tracking system using a calibration device 140. FIG. 1B shows a diagram of an environment including an example of a magnetic tracking system 100 for tracking a tracked object 142. The magnetic tracking system 100 includes a magnetic signal detector 130 (also called receiver 130) coupled to a non-magnetic signal detector 110 (such as a camera) in a calibration device 140. The magnetic tracking system 100 is configured to determine a location of one or more objects 142 (also called tracked objects), shown in FIG. 1B. The location is relative to a transmitter assembly 112 configured to emit a magnetic signal 132 in an environment of the magnetic tracking system.

Generally, the calibration device 140 is configured to detect the magnetic signal 132 emitted by the transmitter assembly 112 and determine a position and orientation (called a pose) of the calibration device 140 in the environment. Based on the position and orientation of the calibration device 140 in the environment, distortions in the magnetic signal can be mapped in the environment for subsequent tracking of the tracked object 142. The calibration device 140 determines, using non-magnetic signals, a location in the environment for the calibration device and determines, for that location, a distortion to the magnetic signal generated by the transmitter 112. A distortion map is generated based on measured distortions at a set of locations in the environment.

Generally, the magnetic signal can be distorted in the environment by objects (called non-tracked objects 120) in the environment other than the tracked objects. The non-tracked objects 120 can include objects such as operating tables, chairs, shelves, or any other metal or magnetically responsive object in the environment. Generally, the magnetic tracking system 100 is calibrated to update the determined pose of the calibration device 140 based on the distortions of the magnetic signal 132 known to be caused by the non-tracked objects 120. The calibration can be performed prior to operation of the magnetic tracking system 100 to track the tracked objects 142. The calibration generates a distortion correction model that indicates, for any location in the environment, a distortion to the magnetic signal 132 caused by the non-tracked objects 120.

For correcting the distortions in the magnetic signal 132 caused by the non-tracked objects 120, the magnetic tracking system 100 uses a non-magnetic signal that is a part of the calibration device 140. The magnetic tracking system 100 uses the non-magnetic signal (e.g., a visual signal) to determine a location of the calibration device 140 in the environment. The magnetic tracking system 100 determines, using the distortion correction model generated during the calibration of the magnetic tracking system 100, a distortion in the magnetic signal 132 caused by the non-tracked objects 120 at the location of the calibration device 140. The magnetic tracking system 100 performs a distortion correction to remove the distortion caused by the non-tracked objects 120 to generate data representing a corrected magnetic signal. The magnetic tracking system 100 determines a position of the tracked object 142 using the corrected magnetic signal.

The magnetic tracking system 100 uses a non-magnetic device to determine a pose of the calibration device 140 in the environment. The non-magnetic device (e.g., non-magnetic signal detector 110) is used for calibration of the magnetic tracking system 100 by generation of the distortion correction model as previously described. The non-magnetic signal detector 110 receives the non-magnetic signal (e.g., a visual signal). The calibration device 140 receives a magnetic signal 132 from the transmitter 112 for the same location in the environment as for the visual signal. The computing device 102, based on the visual signal (e.g., including representations of markers 108) and the corresponding magnetic signal 132 for that location, estimates a pose of the calibration device 140. The magnetic tracking system 100 uses a first pose estimate from the non-magnetic signal (e.g., visual signal detectible by a camera 110) and a second pose estimate from the magnetic signal 132 together to generate final pose estimate for the magnetic tracking device 140. When this is performed in real time, it can be referred to as a fused pose estimate because the magnetic tracking system 100 combines the pose estimates from the magnetic and non-magnetic signals. This would typically be done using a Kalman filter based Simultaneous Localization and Mapping (SLAM) process to perform fusion. An example of this can be found in U.S. Patent Application Pub. No. 2019/0242952, filed on Feb. 8, 2019, and is incorporated in entirely by reference in this document.

Another approach is to collect either 1) a pose estimate from the non-magnetic signal (e.g., a visual signal from camera 110) and a second pose estimate from the received magnetic signal 132 together or 2) the pose estimate from the non-magnetic signal (e.g., from the camera 110) and the distortions in the magnetic signal 132 caused by the non-tracked objects 120. When the poses are collected for both non-magnetic and magnetic signals, a compensation method that corrects the distorted magnetic pose into non-magnetic pose information can be performed. This correction is computed offline but applied in real time to the magnetic pose estimate to perform improved EM tracking. When the non-magnetic pose and magnetic signals are collected, the non-magnetic pose is converted to virtual magnetic signals, and the difference between these and the magnetic signals are used to map distorted magnetic signals into the virtual non-magnetic signals. This mapping is computed offline but applied in real time to the magnetic signals to perform improved EM tracking.

To acquire the non-magnetic signal, the non-magnetic signal detector 110 is moved around the environment 200 to various locations. In FIG. 1A, an example of the non-magnetic signal detector 110 is a camera. However, other non-magnetic signals can be used to determine a ground-truth location of the calibration device 140 in the environment. The camera (and other components of the magnetic tracking system 100) is described in greater detail with respect to FIG. 2. Other examples of non-magnetic signal detectors 110 can include an ultrasonic device, a radio device, an infrared device, an acoustic device, and so forth configured to receive a signal and localize the non-magnetic signal detector 110 using the received non-magnetic signal.

The non-magnetic signal detector 110 can include a camera. The camera can be configured to view markers 106a-e, collectively markers 106, and marker array 108, positioned in the environment in order to determine the pose of the calibration device 140 (which includes the camera) in the environment. The markers 106 and marker array 108 can be optical markers. As the magnetic tracking system 100 (and the camera) are moved around the environment, the field of view 144 of the camera passes across the markers 106a-e and/or marker array 108. The orientation of the markers with respect to one another and to the camera provide information about where the camera is located in the environment. For example, the locations of the each of the markers 106a, 106b, 106c, and 106d, 106e, and the array of markers 108 in the environment are known. When the camera field of view 144 records one of the markers 106a-e or marker array 108 in an image or video, the position and orientation of the marker relative to the camera are discernable from the images or video captured by the camera. The absolute pose of the camera can be discerned using data regarding the positions of each of the markers 106a-e or marker array 108 in the environment and the relative pose of the camera relative to the markers.

In some implementations, the marker array 108 is placed at or near the location of where the tracked object will be during operation of the magnetic tracking system 100. For example, the marker array can be placed on an operating table, operating chair, a floor under the tracked object 142, a ceiling above the tracked object 142, and so forth. In some implementations, the markers of marker array 108 can be placed in a regular pattern, shown in FIG. 1A. In some implementations, the markers of the array 108 can be arranged in irregular patterns that can indicate where in the array the camera is viewing when only a portion of the array is visible. In some implementations, the markers of the array 108 are each unique in one or more aspects, such as the pattern, shape, size, or in another aspect.

The magnetic tracking system 100 can use various localization processes for determining the pose of the camera relative to the markers 106a-e and/or marker array 108. For example, the magnetic tracking system 100 can use a Simultaneous Localization and Mapping (SLAM) process. The SLAM process can use the markers 106a-e and marker array 108 as landmarks. In some implementations, each of the markers 106a-e and markers of marker array 108 are unique such that each is distinguishable from the other markers.

Once the magnetic tracking system 100 has a pose estimate using the non-magnetic signal, the magnetic signal receiver 130 can be used to measure the magnetic signal 132 at the same pose of the calibration device 140 for which that pose estimate was generated. The magnetic tracking system 100 generates another pose estimate using the magnetic signal 132. The pose estimate generated from the magnetic signal 132 is corrected using the pose estimate from the non-magnetic signal. This process can be repeated as the calibration device 140 is moved around the environment.

As shown in FIGS. 1A and 1B, the markers 106a-e and marker array 108 can be placed in a pattern near where the tracked object 142 is to be tracked in the environment. The calibration device 140 can view the markers 106a-e and/or marker array 108. In some implementations, the markers 106a-d can be placed on and around the non-tracked object 120 in the environment. In some implementations, one or more markers, such as marker 106e, can be positioned on the transmitter 112. The calibration device 140 can determine a relative pose with respect to the transmitter 112 by viewing the marker(s) 106e on the transmitter assembly 112.

In some implementations, the calibration device 140 can include a transmitter (such as transmitter 112) and the receiver 130 can be fixed in place in the environment while the calibration device 140 is moved around the environment. This also enables the calibration device 140 to determine its position and orientation in the environment by magnetic means.

In some implementations, the magnetic signal 132 can be transformed directly into pose data from which pose compensation (e.g., distortion compensation) is performed. The pose data from the magnetic signal 134 are compared to the optically determined pose of the calibration device 140 for generating the distortion correction map for the environment.

For simplicity, an example non-magnetic signal detector 110 including a camera is described in detail as an example embodiment throughout this disclosure. However, other non-magnetic signal detector 110 configurations are possible. For example, the non-magnetic signal detector 110 can include a radio signal receiver. Radio beacons (or other radio signal emitters) can be placed around the environment to emit signals that can be used to localize the non-magnetic signal detector 110 in the environment. Other frequencies in the electromagnetic spectrum are also possible.

The processing of the magnetic signal 132 and the non-magnetic signal can be performed by a computing device 102. The computing device 102 can include one or more processors, as subsequently described in relation to FIG. 7. For example, the computing device 102 is configured to receive data representing the magnetic signal 132 and the non-magnetic signal and perform the distortion correction processing for determining the pose of the calibration device 140 and the tracked object 142.

A user interface 104 is configured to be in communication with the computing device 102. The user interface 104 is configured to present a representation of the pose of the calibration device 140, the tracked object 142, and so forth. The user interface 104 can be configured to display a three dimensional representation of the calibration device 140 and tracked device 142 in the environment. Other such representations of the calibration device 140 and the tracked object 142, and other components of magnetic tracking system 100, are possible. For example, the user interface 104 can display a text representation of the pose of the calibration device 140 or other objects in the environment according to a coordinate system (such as a Cartesian system, polar coordinate system, etc.).

The user interface 104 can be configured to present a representation of the distortion correction model determined by the computing device 102 for the environment. For example, a heat map overlay can show which regions in the environment have greater distortions (e.g., with greater heat map values).

The user interface 104 can include a display for reporting the position and orientation of the tracked object to a user of the magnetic tracking system 100. The position and orientation that are reported to the user can be useful for assisting the user in one or more applications, such as performing a medical operation. For example, the user interface can report the position and orientation as a visual representation of the tracked object with respect to a portion of the magnetic tracking system 100, report coordinates of the tracked object, superimpose the tracked object in images captured by the camera 110, and so forth.

The user interface 104 can be configured to control operation of the transmitter assembly 112. The user interface 104 can include one or more controls (software controls, hardware controls, etc.). The controls can be configured to enable the user to turn the transmitter assembly 112 off or on, change the frequency of operation of one or more of the transmitter assemblies, cause a transmitter assembly to upload calibration data, and so forth.

In some implementations, the computing device 102 is configured to send or transmit distortion correction data to one or more other devices. For example, in a medical environment, the computing device 102 can be configured to transmit distortion correction data to one or more other surgical instruments, magnetic tracking devices, visualization generation devices, and so forth.

Turning to FIG. 1B, the magnetic tracking system 100 is shown during tracking of the tracked object 142. The tracked object 142 is moved in the environment of the magnetic tracking system 100. The computing device 102 mapped the distortions based on the data measured by the calibration device 140. The location of the tracked object 142 relative to the transmitter 112 is determine with the distortion effects from the non-tracked objects 120 removed to improve the accuracy of determining where the tracked object 142 is in the environment. The tracked object 142 includes items such as surgical tools or tool tips that are being tracked in the environment. Generally, the calibration device 140 need not be present during tracking of the tracked object 142. While the markers 108 can still be present in the environment, the distortions have already been mapped by the calibration device 140. The markers can be moved from the environment if necessary, such as away from a surgical table or operating area, if the markers interfere with one or more tasks performed during tracking by the magnetic tracking system 100.

Figure 2:
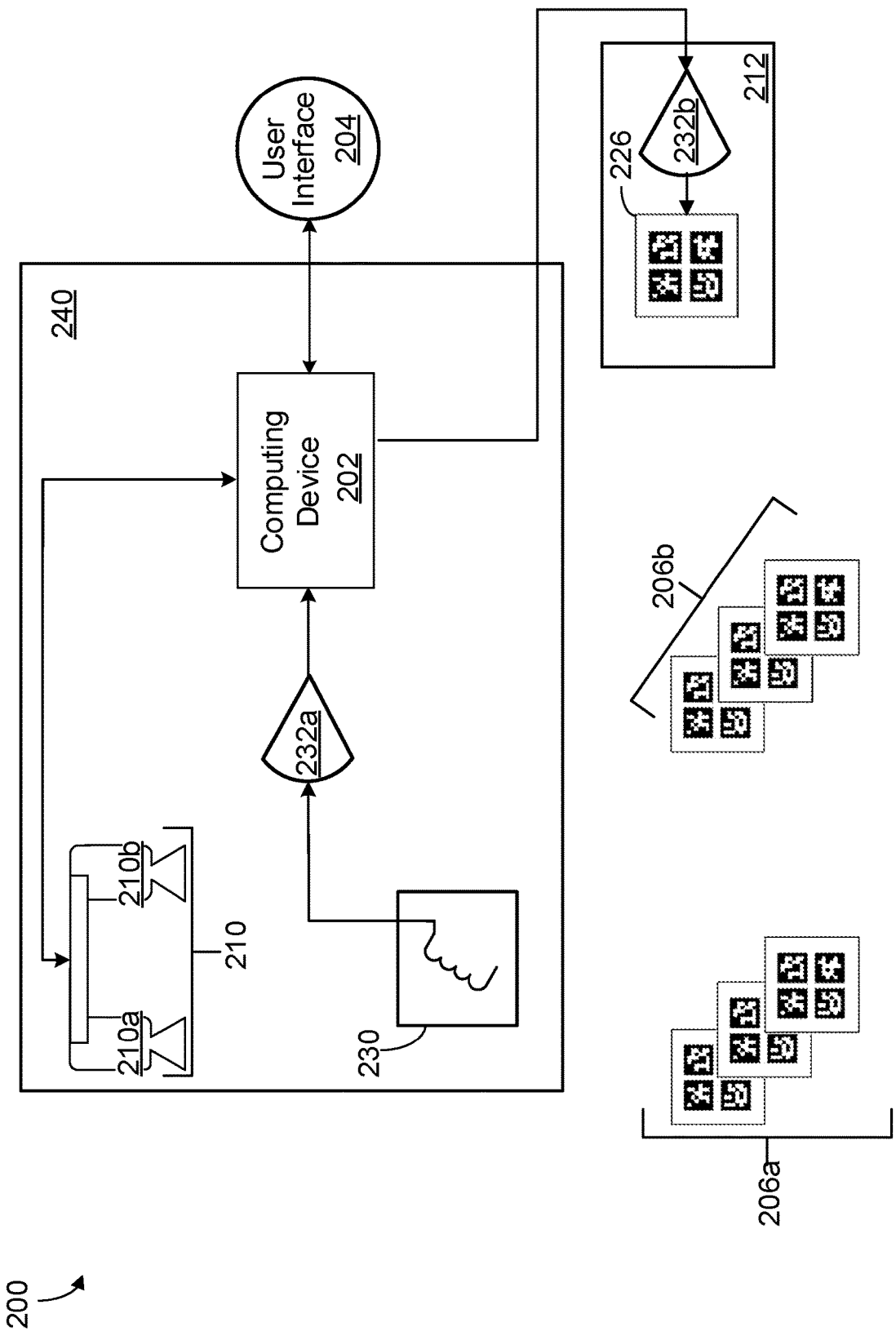
FIG. 2 shows a block diagram of the example magnetic tracking system of FIG. 1.

Turning to FIG. 2, an example of the magnetic tracking system 200 is shown. In some implementations, magnetic tracking system 200 can be similar to magnetic tracking system 100 of FIG. 1A and FIG. 1B. As previously described, the magnetic tracking system 200 includes a computing device 202 (which can be similar to computing device 102 of FIG. 1A and FIG. 1B), a user interface 204 (similar to user interface 104), a camera device 210 (similar to camera device 110), and a transmitter assembly 212, similar to transmitter 112. The magnetic tracking system 200 also includes include amplifiers 232a-b, and the magnetic receiver 230 (also called a receiver assembly 230 or receiver 230). Various embodiments of the components of the magnetic tracking system 200 are now described.

The magnetic tracking system 200 is configured to track the position(s) and orientation(s) of one or more tracked objects (not shown) that are in the environment of the magnetic tracking system 200. In medical contexts, the tracked object generally includes a medical device or a portion of a medical device. For example, the magnetic tracking system 200 can be used to track items such as surgical instruments, probes, endoscopes, catheters, and so forth when they are inside a human body. In some implementations, the magnetic tracking device 240 (similar to calibration device 140 of FIG. 1A) is the tracked object. In some implementations, the tracked object is another object, and the magnetic tracking device 240 is used for distortion correction only. The magnetic tracking device 240 includes the receiver 130 that senses the magnetic signal 132 from the transmitter assembly 212. The magnetic tracking system 200 can determine the position of the receiver 230 of the tracked object based on these signals, as subsequently described in greater detail.

The magnetic tracking system 200 is configured to emit a magnetic signal (e.g., a magnetic field) from the transmitter assembly 212. The receiver 230 is configured to measure the magnetic field and send the measured signal to the computing device 102. In some implementations, an amplifier 232 is included to amplify the signal that is measured by the receiver 230. The amplifier 232 generally has a positive gain configured to amplify any analog signals received from the receiver 230 so that the computing device 202 can receive the amplified signal as an input. The receiver 230 can include one or more elements for measuring the magnetic signal emitted by the transmitter assembly 212, such as a magnetometers, coils, etc. For performing tracking of the tracked object, the position and orientation of the receiver 230 is calculated by computing device 202 using measurements of the fields from the transmitter assembly 212. The position and orientation of the transmitter assembly 212 are known by observing the transmitter assembly 212 with cameras 210a-b or equivalent non-magnetic sensor.

The transmitter assembly 212 includes a transmitting element configured to generate a magnetic signal, such as a transmitter coil. In some implementations, multiple distinct transmitter assemblies can be used. The transmitter assemblies can be slightly different (or even unique) from one or more of the other transmitter assemblies. For example, the transmitter assembly 212 can be configured to transmit a magnetic signal using a different modulating frequency. In some implementations, each coil has slightly different magnetic properties. The computing device 202 can store information characterizing the magnetic properties of the transmitter assembly 212 for calibration purposes. In some implementations, the transmitter assembly 212 includes markers 226 (similar to markers 206) that can be used for optically determining the location of the transmitter assembly relative to the camera 210 or tracking device 240.

During operation of the magnetic tracking system 200, the transmitter assembly 212 is configured to emit a magnetic signal that can be measured by the receiver 230.

In some implementations, the transmitter assembly 212 is configured to be identifiable by a non-magnetic means to determine the position and orientation the transmitter assembly with respect to the magnetic tracking device 240. The non-magnetic means can include one or more of an optical means, an ultrasonic means, a radio means, acoustic means, infrared means, and so forth. Generally, one or more of the markers 206a-b (which can be similar to markers 106a-e and/or marker array 108), such as an optical or fiducial marker, can be included on or near the transmitter assembly 212. The computing device 202 is configured to recognize the marker, distinguish the marker from other markers, and determine a potion and orientation of the marker (and thus the position and orientation of a transmitter assembly) from images of the marker. While markers 206a and 206b appear as groups of markers in FIG. 2, each marker 206a and 206b can be an individual marker.

While the markers 206a-b can be placed on the transmitter itself, the markers can also be placed throughout the environment. One or more of the markers 206a-b can include unique patterns such that each marker is distinct from other markers in the environment. Generally, the markers 206a-b are positioned such that, at any given pose used for distortion correction, the camera 210a-b field of view includes at least one marker. The magnetic tracking system 200 is configured to optically determine the pose of the magnetic tracking device 240 (which includes the camera 210, the computing device 202, and the receiver 230). The optically determined pose is used to determine the distortions that are present in the magnetic signal 132 received by the receiver, as previously described. For example, in a medical context, the camera 210 is placed above the patient and the markers 206a-b (e.g., including 106a-e and/or marker array 108) are placed around where the patient surgery will be (e.g., a region where distortions are being mapped). The camera 110 is configured to capture images of the markers 206a-b (e.g., including markers 106a-e and/or marker array 108) to measure, for each pose of the magnetic tracking device 240, a corresponding magnetic signal 132. This measured magnetic signal 132 can be compared to an ideal magnetic signal that would be present without distortions. The difference in the magnetic signals can be used to generate, for each pose in the region, a distortion value. The distortion values are determined for each pose in the region with a resolution that is acceptable for the application being performed (e.g., a surgery). For example, the magnetic tracking device 240 can be moved an inch, two inches, five inches, etc. between measurements. For example, the magnetic tracking device 240 can be rotated 1 degree, 2 degrees, 5 degrees, etc. as needed between measurements.

In some implementations, the camera 210 is removed (or not included) for performing magnetic tracking during operation of the magnetic tracking device 240. For example, during a surgery, the camera 210 can be disconnected from the magnetic tracking device 240.

In some implementations, the camera 210 can be a stereoscopic camera including two cameras, such as camera 210a, and camera 210b that are displaced from one another. The cameras 210a, 210b are configured to capture images from different angles with respect to the markers 206a-b. The images from the stereoscopic cameras 210a, 210b can be used to determine not only planar "x, y" position data and yaw of the magnetic tracking device 240, but also the depth "z" position of magnetic tracking device 240 and the roll and pitch of the magnetic tracking device with respect to the markers 206a-b. In some implementations, a single camera is used to determine depth data using multiple markers 206 on a same object (e.g., spaced at a known distance from each other).

The data representing the relative positions and orientations of the magnetic tracking device 240 are used by the computing device 202 to determine how to interpret the magnetic signals received from the receiver 230. The magnetic signals indicate a position and orientation of the tracked device relative to the transmitter assembly 212. To determine the absolute position and orientation of the tracked device, the positions and orientations of the markers are determined. Generally, each of the markers has a known position and orientation with respect to the transmitter assembly 212. The coordinate system established by these markers is the global coordinate system (e.g., the Cartesian coordinate axes shown in FIG. 1A and FIG. 1B).

The receiver 230 is configured to measure the magnetic signals transmitted by the transmitter assembly 212 to determine the position and orientation of the tracked object with respect to the transmitter assemblies. The position of the tracked object can be measured as relative to any global reference point, such as the transmitter assembly 212. The computing device 202 is configured to convert the measured magnetic signals into position and orientation data. In some implementations, position data can be expressed as a position vector of position coordinates (e.g., x, y, z coordinates). In this example, the receiver 230 uses a Cartesian coordinate system (with x, y, and z coordinates) to represent a location in space; however, other types of coordinate systems (e.g., cylindrical, spherical, etc.) may be utilized.

The orientation of the tracked object refers to a direction the tracked device is facing with respect to the global reference point (e.g., the transmitter assembly 212), and can be expressed similarly by using a coordinate system and represented, for example, as a vector of orientation coordinates (e.g., azimuth ($\Psi$), altitude ($\theta$), and roll ($\varphi$) angles). The magnetic tracking system 200 operates to be an up to six degree of freedom (6 DoF) measurement system that is configured to allow for measurement of position and orientation information related to a forward/back position, up/down position, left/right position, azimuth, altitude, and roll. For example, if the receiver 230 includes a single receiving coil, a set of minimum of at least five transmitter assemblies 212 can provide five degrees of freedom (e.g., without roll). In an example, if the receiver 230 includes as least two receiving coils, a minimum of at least six transmitter assemblies 212 can provide enough data for all six degrees of freedom to be determined. Additional transmitter assemblies or receiving coils can be added to increase tracking accuracy or allow for larger tracking volumes.

The computing device 202 comprises one or more processors and is configured to receive data representing the magnetic signal 132 and the non-magnetic signal for estimating the distortion of the magnetic signal in the environment. The computing device 202 receives the magnetic signal from the receiver 230 and converts the magnetic signal into position data and orientation data of the magnetic tracking device 240. The computing device 202 can include input and output ports for sending and receiving both analog and digital data. The computing device 202 can include a waveform generator (not shown) for driving the transmitter assembly 212. Aspects and examples of the computing device 102 are further described in relation to FIG. 7.

The computing device 202 can include circuitry to drive the transmitter assembly 212 and control the operation of the transmitter assembly 212. For example, the computing device 202 can include a controller that is configured to control the transmitter assembly 212. The transmitter assembly 212 can be configured to emit magnetic signals at different times or frequencies in a measurement cycle. For example, the computing device 202 can be configured to control the transmitter assembly 212 to transmit a magnetic signal at a particular time in a measurement cycle, transmit magnetic signal in a particular sequence, etc. The receiver 230 measures each of the magnetic signals. If a timing regime is used, the computing device 202 can associate the received magnetic signal with a particular transmitter assembly based on when the magnetic signal is received by computing device 202 from the receiver 230. The controller can control the transmitter assembly 212 using time-slice multiplexing, frequency multiplexing, and so forth.

The transmitter assembly 212 can be calibrated individually. In some implementations, the transmitter assembly 212 has one or more physical properties that are distinct. For example, the transmitter assembly 212 can be calibrated with modeled parameters, mapping of magnetic fields from the magnetic signals, spherical harmonics, closed form solutions, and so forth. The calibration data can be stored by the computing device 202. The calibration data for a transmitter assembly can be stored locally with that respective transmitter assembly on a local storage. In an aspect, the calibration data can be sent (e.g., wired or wirelessly) to the computing device 202 to assist the computing device 202 for determining the position and orientation of the transmitter assembly. As stated previously, the transmitter assembly 212 can be configured to operate on a different frequency from one another, turn on at different times, and so forth.

A transmitter coil (not shown) is configured to produce a magnetic signal that is received by the receiver 230. The coil can emit a signal (e.g., magnetic field) that is unique to the particular transmitter assembly 212. For example, the transmitter assembly 212 may modulate the magnetic signal with a particular frequency. The coil can be a single or multi-turn coil. The coil can include any geometric shape capable of generating a magnetic field when supplied with an electric current. The coil can be a part of circuitry of the transmitter assembly 212 (e.g., a printed circuit board (PCB), or the coil can be separately attached to the transmitter assembly.

The transmitter assembly 212 may not include active circuitry. The coil can be driven from a remote source, such as a waveform generator of the computing device 202. The transmitter assembly 212 can be configured to be plugged into the computing device 102 (or another device) to drive the magnetic signal. In some implementations, the transmitter assembly 212 can be configured to connect to one or more other transmitter assemblies, such as in a daisy-chain formation. In another example, the transmitter assembly 212 can be connected in parallel with one or more other transmitter assemblies.

The computing device 202 can be configured to determine the position and orientation of the tracked object in a variety of ways. For example, a least-squares solution can be used to determine the position and orientation of the receiver 230 with respect to the transmitter assembly 212. In another example, a Kalman filter or one or more other numerical methods can be used to determine the positions and orientations of the receiver 230 with respect to the transmitter assembly 212.

The computing device 202, the transmitter assembly 212, the camera 210, and the user interface 204 can communicate with each other through either wired or wireless connections. For example, the transmitter assembly 212 can be wired into ports of the computing device 202. In such a configuration, the computing device 202 can provide a power signal to drive the transmitter assembly 212, and the transmitter assemblies can each include passive electronics. In another example, the transmitter assembly 212 can be equipped with a data transceiver configured to wirelessly transmit data (e.g., calibration information) to the computing device and receive data (e.g., control signals) from the computing device 202.

The markers 206a-b can be rearranged during for distortion correction for the magnetic tracking system 200, and the new positions and orientations of each of the makers can be determined by the computing device 202 using camera 210 data. For example, the markers 206a-b (e.g., including 106a-e and/or marker array 108 of FIG. 1A) can be moved around during calibration to ensure that one or more of the markers is within several inches of where the tracked object (e.g., a catheter) will be while the tracked object is moved around the environment (e.g., inside the patient). Once the markers 206a-b are in place in the environment, the calibration device 140 is moved around the environment to calibrate the distortion correction model for the region.

In some implementations, the markers 206a-b each include adhesive patches which can be affixed to one or more surfaces of the environment of the magnetic tracking system 200. For example, the markers 206a-b can be affixed to a subject (e.g., a patient) of a medical operation.

The combination of the receiver 230 and the transmitter 212 can be a distortion indicator or distortion correction system for the environment. The magnetic tracking system 200 can use a determined difference between optical determination of the optical pose of each of assemblies and the EM determination of pose as an indication of distortion present in the environment. The magnetic tracking system 200 can thus perform distortion compensation. For example, data collected by the receiver assembly 230, including magnetic field measurements and pose, distorted data, optical data (truth), and gradient data (estimated by differences in fields as sensor move) can be used to make corrections for distortion. The distortion can be modeled using physical models. These models can include curve-fitting (e.g., for magnetic signals and for pose solutions), splines, triangulations, radial basis functions, and using machine learning methods.

Figure 3:
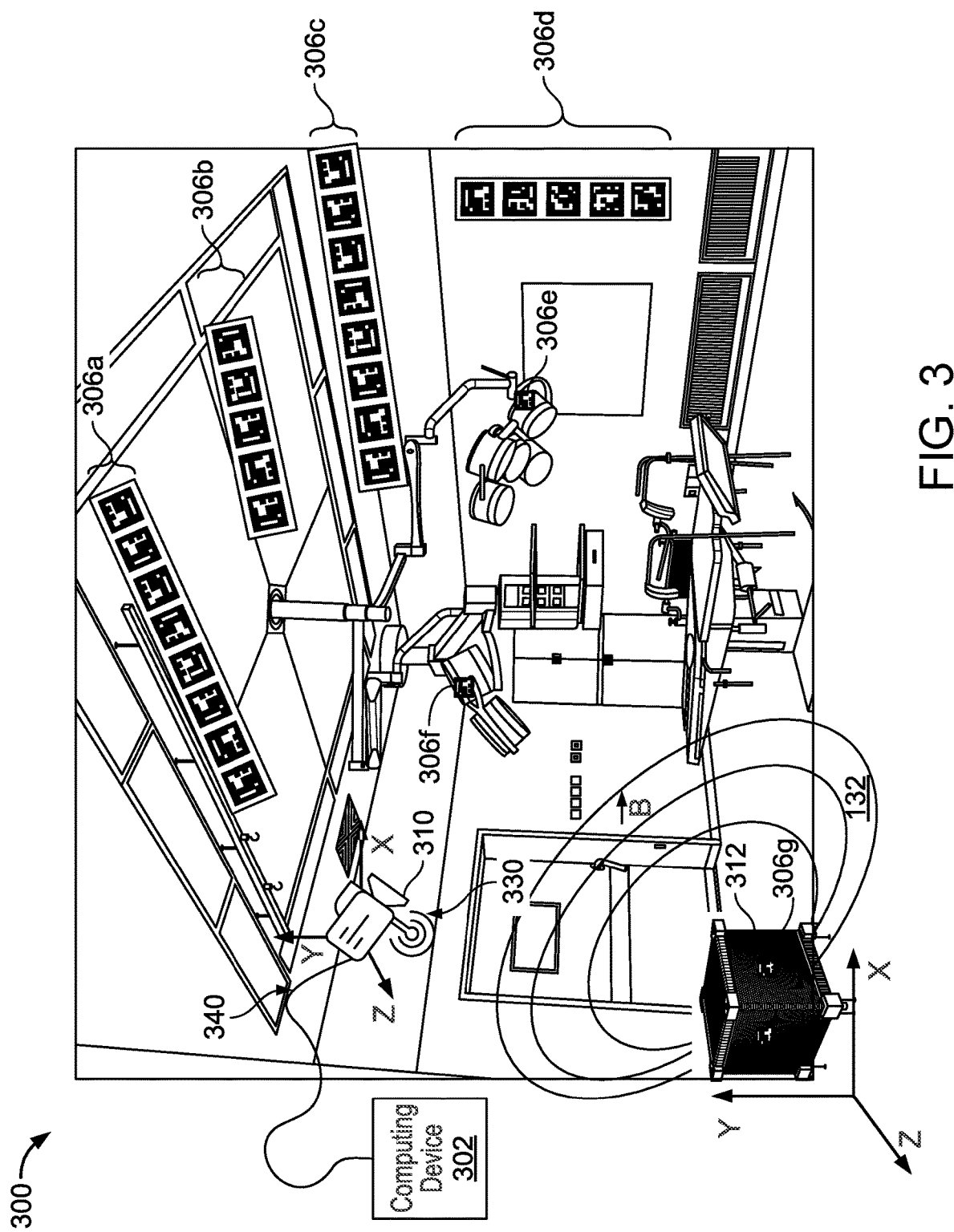
FIG. 3 shows a diagram of an environment including an example of a magnetic tracking system.

Turning to FIG. 3, an example of an environment 300 is shown for distortion correction of the magnetic signal 132. Markers 306a-g (collectively markers 306) are placed throughout the environment 300. The markers 306 can be arranged or rearranged depending on wherein the environment 300 the distortion correction is being performed, similar to markers 106 and 206, previously described. Generally, the markers 306 are placed such at least one is visible to the camera 310 (which can be similar to camera 110 of FIG. 1A and/or camera 210 of FIG. 2) of a magnetic tracking device 340 (similar to magnetic tracking devices 140 and/or 240) at any pose of the magnetic tracking device.

In an aspect, the one or more markers 306 can include any visual mechanism for distinguishing the markers from each other. The markers 306 are each be distinct from one another so that the computing device 302 (which can be similar to computing devices 102 and 202, previously described) can discriminate between the markers when determining the pose of the magnetic tracking device 340 visually. The positions of the markers 306 relative to one another indicate to the computing device 302 what the position and orientation of the transmitter assembly 312 is relative to the camera 310, receiver 330 (e.g., similar to receiver 130 and/or receiver 230, previously described), or other portion of the magnetic tracking system 300. For example, if marker 306b appears in a positive direction along a x-axis with respect to icon 306c, the computing system can determine that the transmitter assembly 300 is rotated at a particular yaw value (e.g., planar rotation with respect to the camera 310). Alternatively, computer vision or machine learning methods may be used to track the transmitter assembly 300, as is known in the art. Each of the markers 306 can be selected from a library of icons which the computing device 302 is configured to recognize and assign to different locations in the environment 300. The computing device 302 associates a received magnetic signal with a position determined based on what marker 306 is seen and what its orientation is. This assists in position and orientation calculations. In other words, the computing device 302 uses the markers 306 to know which magnetic pose is associated with which visual pose. The computing device 302 can then determine what the ideal magnetic signal would be at the ground truth location and determine a magnetic distortion value.

In an aspect, the camera device 310 can include stereoscopic cameras which provide distance information to the computing device 302. The computing device 302 can use the distance information (whether determined at the camera device 310 or calculated at the computing device 302) to determine the position of the transmitter assembly 300 in three dimensions. The camera device 310 can include a single camera which can determine distance based on the use of multiple markers 306a-h and their known geometry.

As stated previously, the markers 306a-h are generally configured to be recognized for computer vision recognition (similar to markers 106 and 206 and marker array 108). The markers can include any images, such as bar codes, QR codes, symbols, icons, and so forth. In the example of magnetic tracking system 300, the markers 306a-h are pixelated symbols. While fewer than 8 symbols are included in this example for each marker 306, additional symbols can be added for determining pose. In addition to being symbols, a marker can include a retroreflector configured for infrared excitation or another kind of landmark that is detectable by a non-magnetic means.

In some implementations, the markers 306a-h can vary, as long as the configuration is capable of providing enough information for the magnetic tracking system 300 to generate an estimate of the visual pose. For example, the markers can include ArUco or ChArUco patterns. For example, the markers can include passive retroreflectors that respond to infrared (IR) excitation from an IR source near the camera aperture(s) 110a and 110b. The markers 306a-f can include active beacons that transmit light signals, radio frequency data, ultrasonic signals, or other pose information. In some implementations, the shapes of the markers 306a themselves can be used for pose determination.

In an aspect, each marker 306a-f can include an adhesive layer which is applied to a side. The adhesive layer is configured to adhere the marker 306 to another surface, such as a wall, ceiling, non-tracked object, and so forth. The surface is not required to be flat or regular. The adhesive layer can include an adhesive gel, glue, suction cups, or other adhesive surface. The adhesive layer is generally configured to be removable and reapplied to a surface repeatedly. The adhesive layer does not obscure the side of the marker 306 that includes the symbols.

Figure 4A:
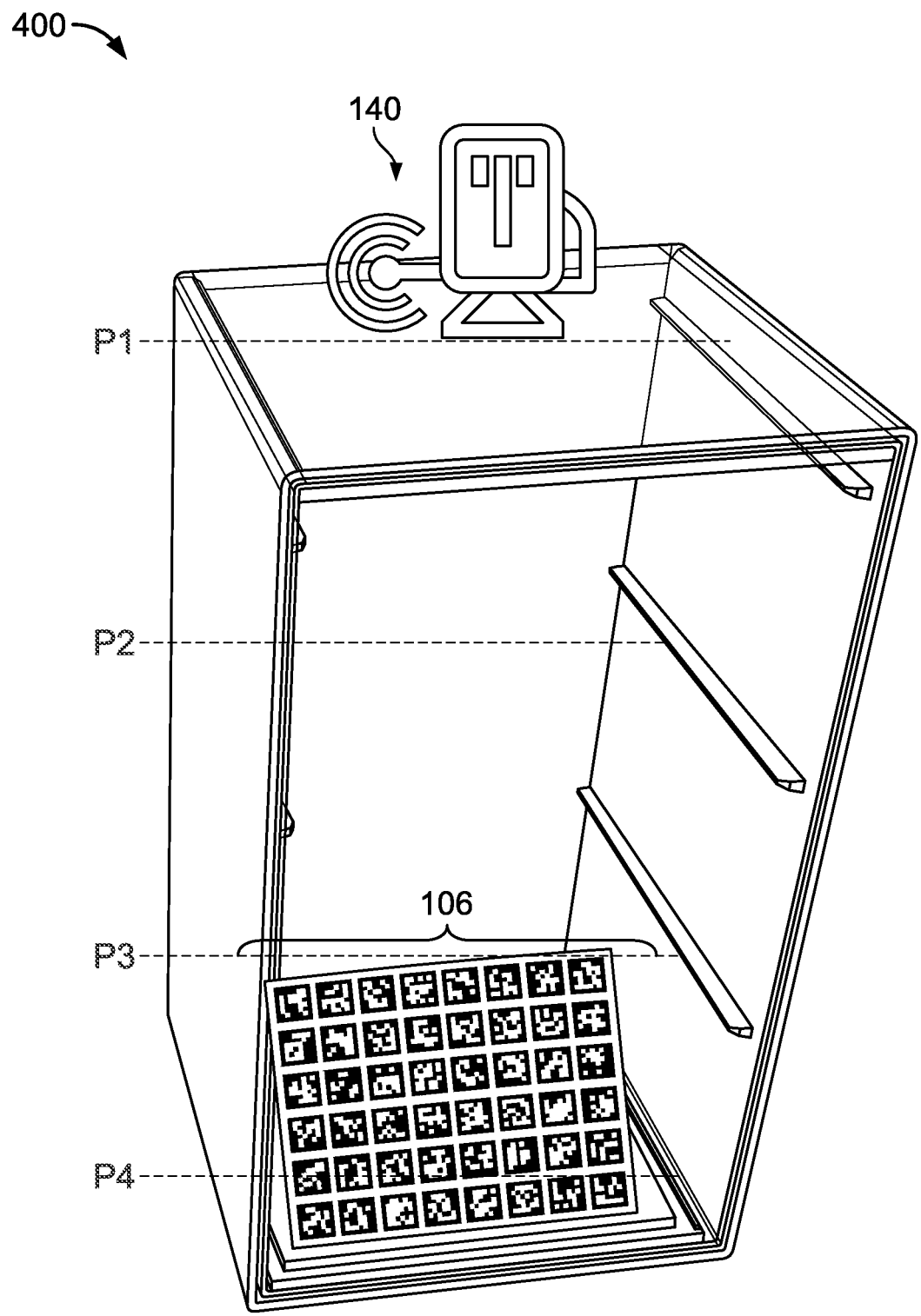
Figure 4B:
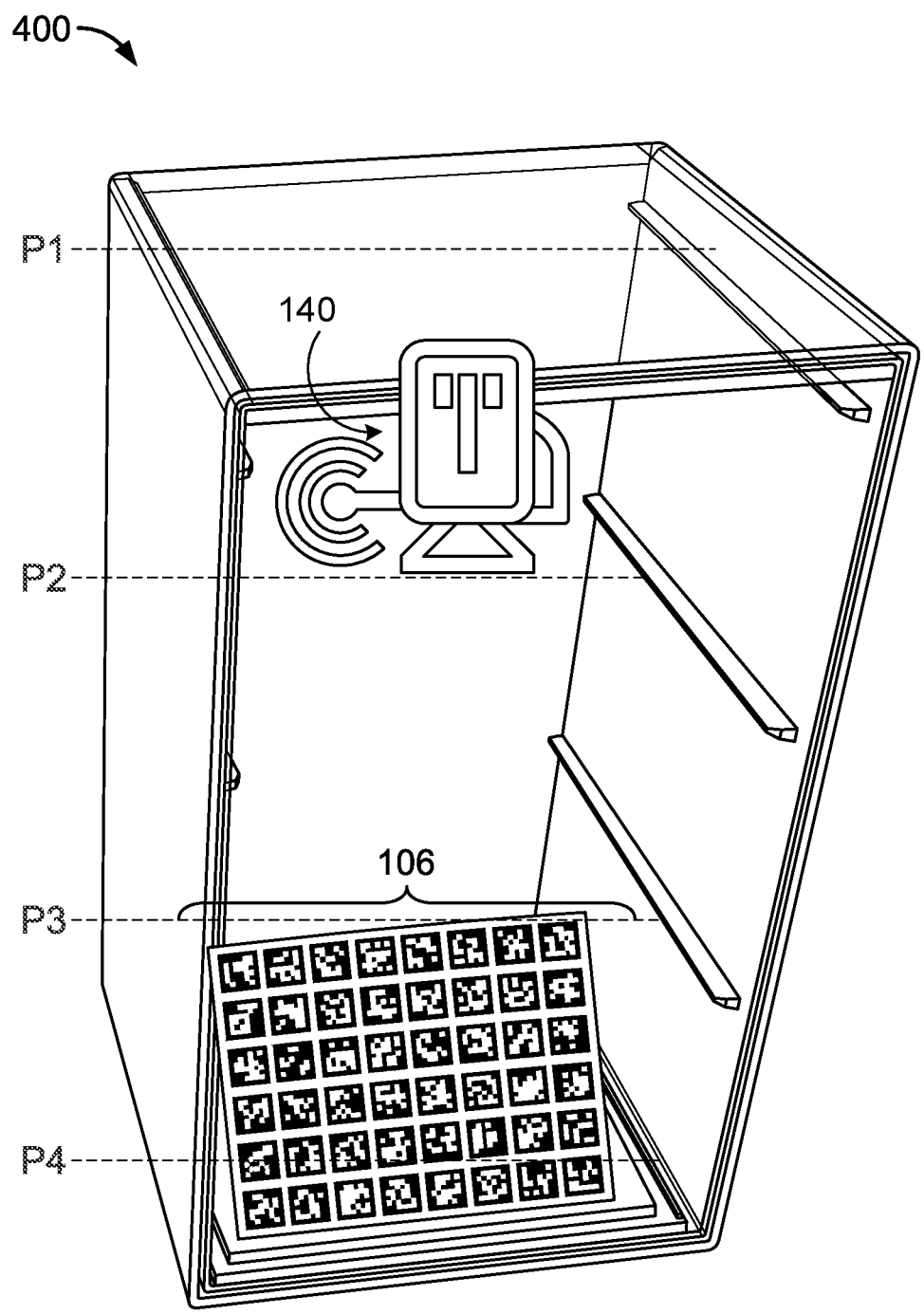

Turning to FIGS. 4A-4B, a calibration environment with a scaffold 400 is shown. The scaffold allows the magnetic tracking device 440 (e.g., similar to magnetic tracking devices 140, 240, and/or 340) to move in a known region of the environment with respect to the markers 406 (similar to markers 106, 206, and 306, previously described). For example, the scaffold 400 allows planar motion of the magnetic tracking device 440 with respect to the markers 406. A number of planes P1, P2, P3, P4, P5 (and so forth) can be provided in the scaffold 400. At each plane, the magnetic tracking device 440 can be positioned and a magnetic signal 132 measured. The pose of the magnetic tracking device 440 is known with a high precision due to the fixed nature of the scaffold 400. Shelves (or other support means) can be added or removed to allow the magnetic tracking device 440 to move relative to the markers 406. Various measurements of the magnetic signal 132 can be taken at each of the planes. A distortion correction model can then be generated as previously described. For example, in FIG. 4A, the magnetic tracking device 440 is at position P1. In FIG. 4B, the magnetic tracking device 440 is at position P2. The planes can be positioned close together to increase a resolution of the distortion correction model as needed. The magnetic tracking device 440 can be moved around the plane to capture a large number of magnetic signal measurements at the plane.

Turning to FIG. 5, a calibration environment with a scaffold 500 is shown. The scaffold includes stackable layers 504 that can be built up or broken down quickly, such as over a patient on a surgical table. The scaffold 500 is portable and allows the magnetic tracking device 502 (e.g., similar to magnetic tracking devices 200, 300) to move in a known region of the environment with respect to the transmitter 112. For example, the scaffold 500 allows planar motion of the magnetic tracking device 502 in the environment. Rather than including markers, the scaffold can be formed with precise dimensions such that the absolute position of the magnetic tracking device 502 is known in a longitudinal direction. An encoder (e.g., a laser-based encoder) can be used to track where the magnetic tracking device 502 moves around the plane. For example, a computer mouse coupled to a receiver (similar to receivers 130, 230, and/or 330) can be used to measure the magnetic signal 132 at each location on a plane. For each plane, the magnetic tracking device 502 can be iteratively positioned across various points on the plane, and the magnetic signal 132 is measured at each point. The pose of the magnetic tracking device 502 is known with a high precision due to the fixed nature of the scaffold 500. Shelves (or other support means) can be added or removed to allow the magnetic tracking device 502 to move in additional dimensions. A distortion correction model can then be generated as previously described. The magnetic tracking device 502 can be moved around the plane to capture a large number of magnetic signal measurements at the plane.

Figure 6A:
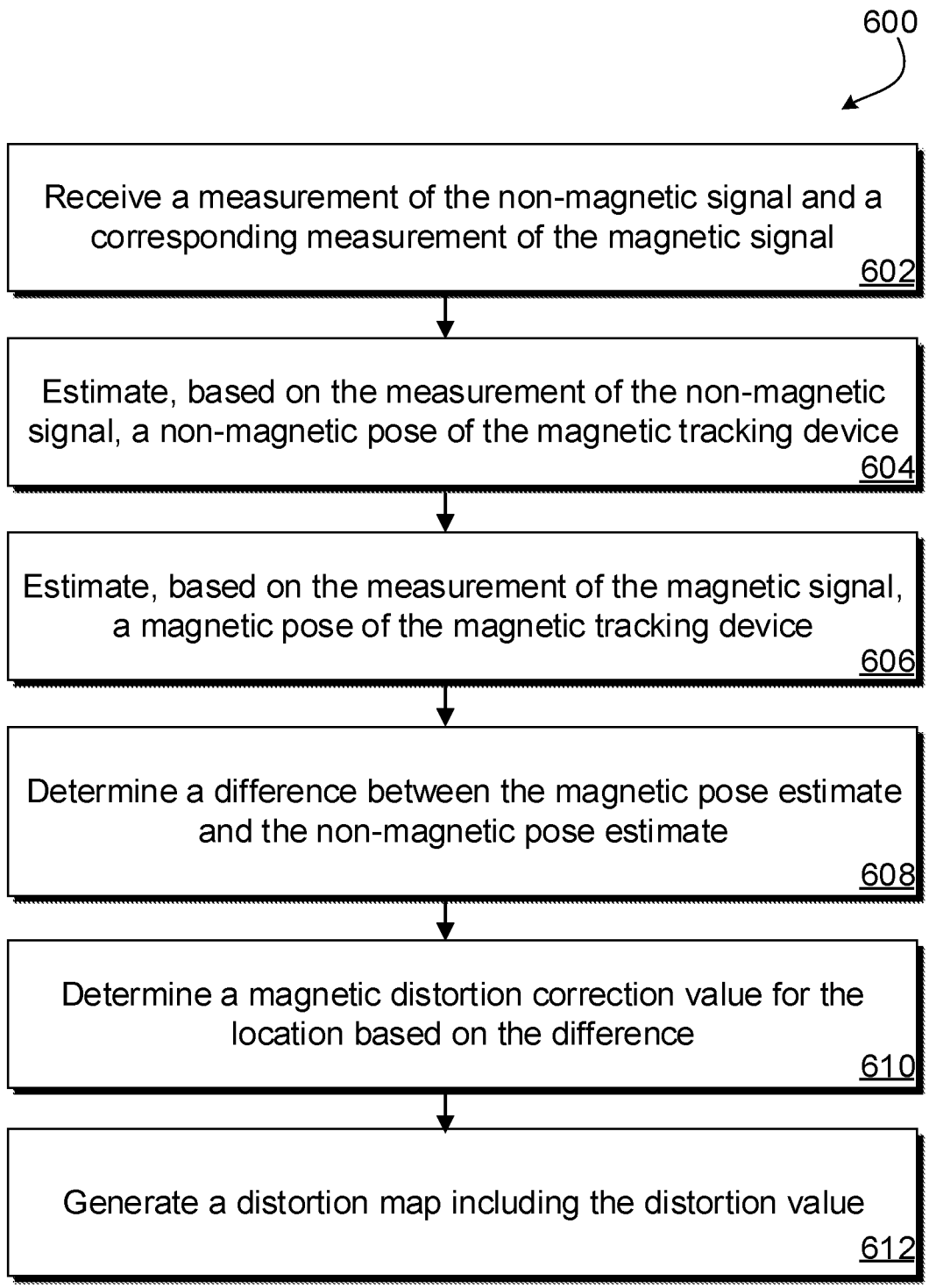
FIGS. 6A-6C are flow diagrams of processes for performing magnetic tracking with the magnetic tracking systems of FIGS. 1-5.

Turning to FIG. 6A, a flow diagram of a process 600 for performing magnetic tracking with the magnetic tracking systems and transmitter assemblies of FIGS. 1-5 is shown. The process 600 represents how a magnetic tracking system (e.g., magnetic tracking systems of FIGS. 1-5) is configured for determining an object pose of a tracked object in an environment of the magnetic tracking system.

A computing system is configured to receive (602), from a magnetic tracking device, a measurement of a non-magnetic signal and a corresponding measurement of the magnetic signal. The non-magnetic signal can include a visual signal, such as an image or video. The computing system estimates (604), based on the measurement of the non-magnetic signal, a non-magnetic pose of the magnetic tracking device in the environment for the location. The computing system is configured to estimate (606), based on the measurement of the magnetic signal, a magnetic pose of the magnetic tracking device in the environment for the same location in the environment. In some implementations, the magnetic pose and the visual pose are estimated in parallel. In some implementations, estimated poses can be saved to buffers for pipelining the generation of the distortion correction model. For example, the computing system determines (608) a difference between the magnetic pose estimate and the non-magnetic pose estimate to produce an error value. As the difference is being determined, the computing system can be configured to measure a next iteration of magnetic signals and non-magnetic signals to estimate a second magnetic pose and a second non-magnetic pose.

The computing system is configured to determine (610) a magnetic distortion correction value for associating with the particular location in the environment based on the determined difference in the pose values. Once distortion values are calculated for a plurality of locations, the computing system can build or generate (612) a distortion correction model may be formed with distortion models, spherical harmonics, mathematical functions and the like and can be performed using a pre-computed correction or as evaluating a model in real time, including the distortion values and output a representation of the distortion correction model. The distortion correction model can be stored in a memory such that, as the magnetic tracking system is moved around an environment, the distortion correction can be retrieved to correct a magnetic pose that is determined by the magnetic tracking system. In other words, because the distortion value for a given location in the environment is known, the magnetic tracking system can refine the magnetic pose estimate of the tracked object once object tracking is performed. During tracking, the computing device is configured to output a representation of the tracked object pose, such as to a user interface.

In some implementations, the marker comprises one of an ArUco pattern, a ChArUco pattern, an infrared retroreflector, a light source, an ultrasonic source, a radio signal source, and an outer shape of the transmitter assembly.

Figure 6B:
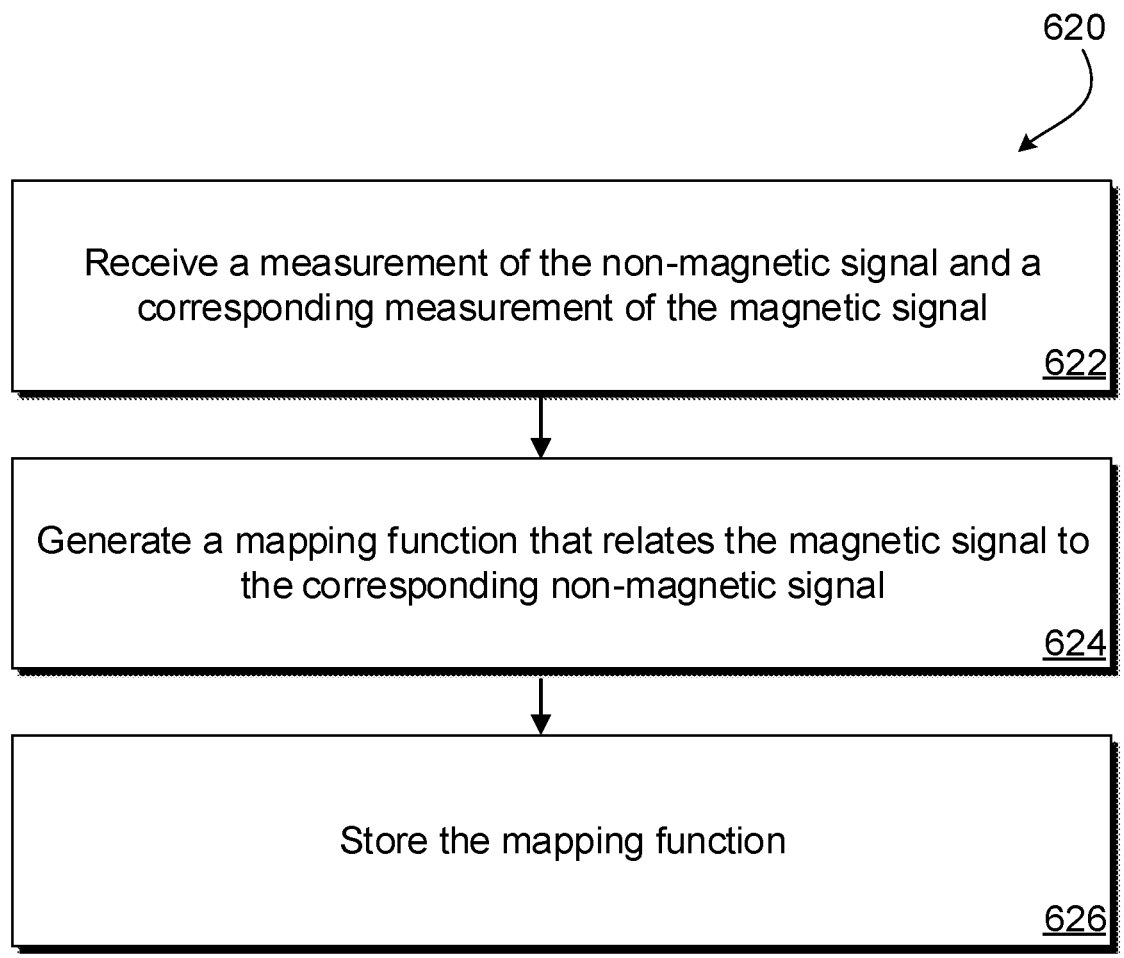

FIG. 6B shows a process 620 for distortion correction for electromagnetic fields using inside-out tracking. Process 620 illustrates a function fitting process where a non-magnetic signal is a function of the magnetic signal. For example, the x position of the magnetic signal may be compensated by a polynomial comprised of powers of the magnetic signal such that it equals the non-magnetic signal. These functions take many forms, such as polynomials, radial basis functions, spherical harmonics, kriging, neural networks, splines, etc. The function fitting process is typically performed off-line after all the signal data is captured. The magnetic signal may be in the measurement domain (the magnetic fields) ad/or the tacking (solution or pose) domain.

A computing device (such as computing devices 102, 202, or 302 of FIGS. 1-3) is configured to receive (622) a measurement of the non-magnetic signal and a corresponding measurement of the magnetic signal. The computing device is configured to generate (624) a mapping function that relates the magnetic signal to the corresponding non-magnetic signal. The computing device is configured to store (626) the mapping function for use during magnetic tracking.

Figure 6C:
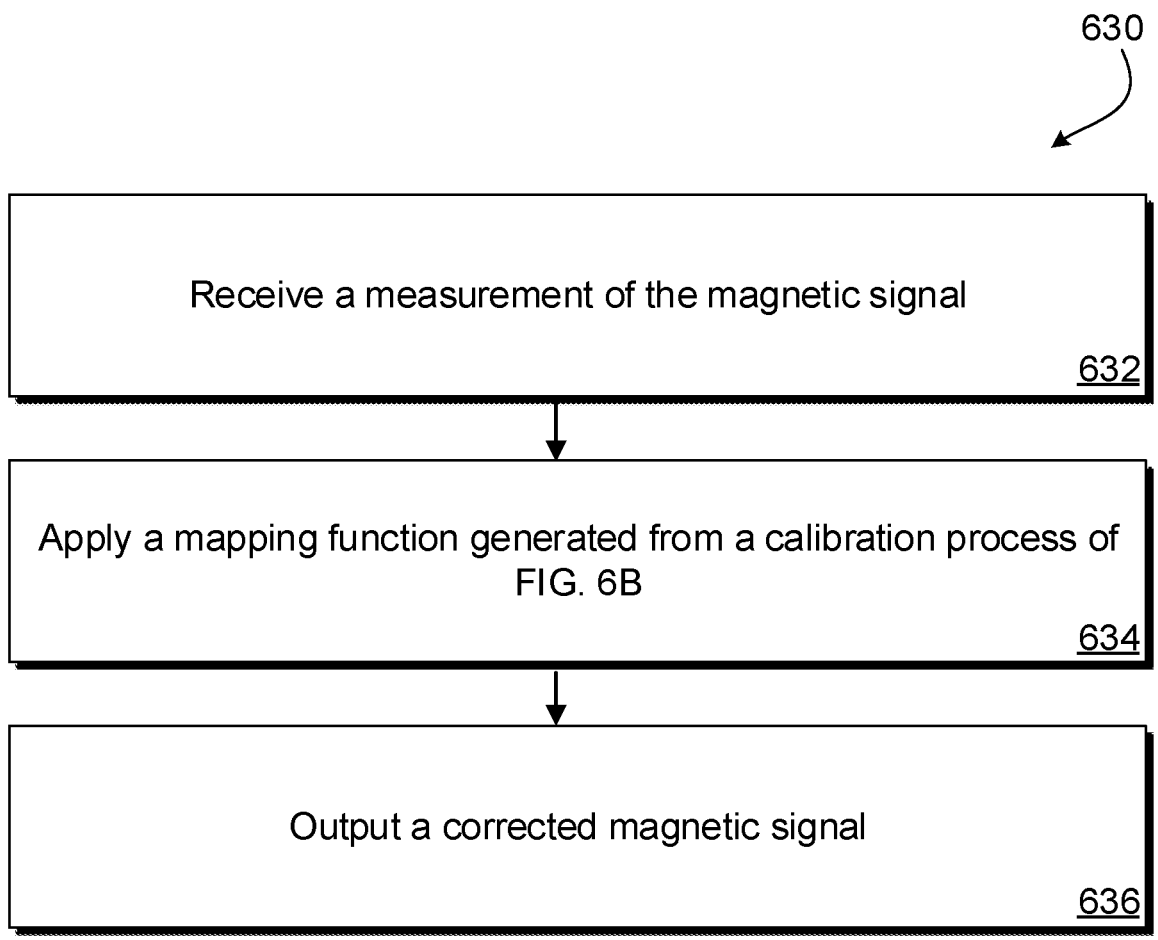

FIG. 6C shows a process 630 for distortion correction for electromagnetic fields using inside-out tracking. Process 630 illustrates the process of using the function generated by process 620 during EM-only tracking. A magnetic signal is received, and that signal is used in the function to generate a corrected magnetic signal. The corrected magnetic signal may be in the measurement domain (the magnetic fields) and/or the tacking (e.g., solution or pose) domain. If the corrected magnetic signal is in the measurement domain, the corrected magnetic signal is then run through the standard tracking algorithm to generate pose data.

A computing device (such as computing devices 102, 202, or 302 of FIGS. 1-3) is configured to receive (632) a measurement of the magnetic signal during a tracking process. The computing device is configured to apply (634) a mapping function generated from a calibration process of FIG. 6B to the received signal. The computing device is configured to output (636) a corrected magnetic signal indicating the true location and orientation of the tracked device.

Figure 7:
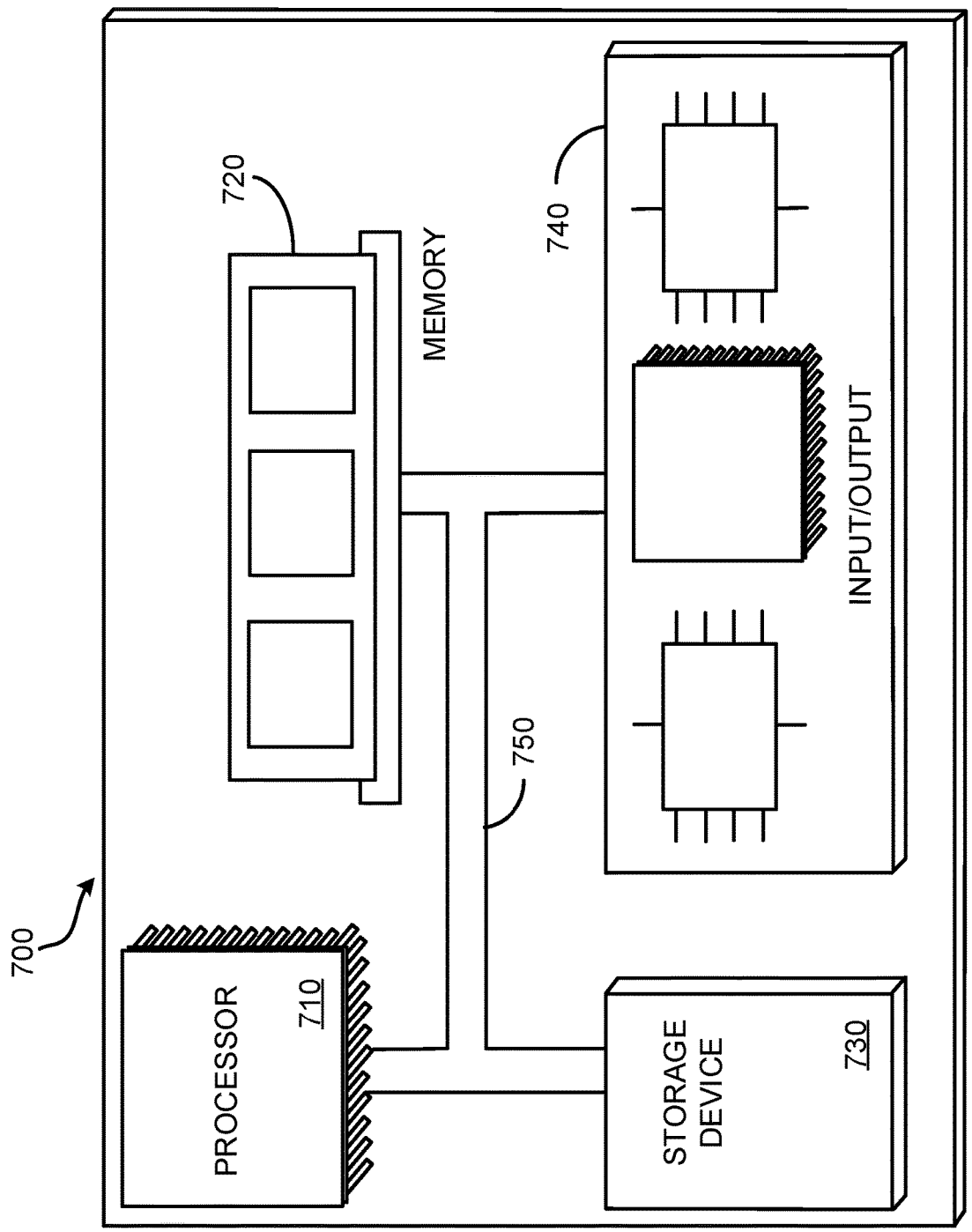
FIG. 7 is a block diagram of an example computer system.

FIG. 7 is a block diagram of an example computer system 700. The computing device 102 of FIGS. 1A-1B may be an example of the computer system 700 described here. The system 700 can include a processor 710, a memory 720, a storage device 730, and an input/output device 740. Each of the components 710, 720, 730, and 740 can be interconnected, for example, using a system bus 750. The processor 710 is capable of processing instructions for execution within the system 700. The processor 710 can be a single-threaded processor, a multi-threaded processor, or a quantum computer. The processor 710 is capable of processing instructions stored in the memory 720 or on the storage device 730. The processor 710 may execute operations such as causing the EMT system 100 to determine the position and/or the orientation of tracked device 102.

The memory 720 stores information within the system 700. In some implementations, the memory 720 is a computer-readable medium. The memory 720 can, for example, be a volatile memory unit or a non-volatile memory unit.

The storage device 730 is capable of providing mass storage for the system 700. In an aspect, the storage device 730 is a non-transitory computer-readable medium. The storage device 730 can include, for example, a hard disk device, an optical disk device, a solid-date drive, a flash drive, magnetic tape, or some other large capacity storage device. The storage device 730 may alternatively be a cloud storage device, e.g., a logical storage device including multiple physical storage devices distributed on a network and accessed using a network. In some implementations, the information stored on the memory 720 can also or instead be stored on the storage device 730.

The input/output device 740 provides input/output operations for the system 700. In some examples, the input/output device 740 includes one or more of network interface devices (e.g., an Ethernet card), a serial communication device (e.g., an RS-232 10 port), and/or a wireless interface device (e.g., a short-range wireless communication device, an 602.11 card, a 3G wireless modem, or a 4G wireless modem). Generally, the input/output device 740 includes driver devices configured to receive input data and send output data to other input/output devices, e.g., a keyboard, a printer, and display devices. In some implementations, mobile computing devices, mobile communication devices, and other devices are used.

The system 700 can include a microcontroller. A microcontroller is a device that contains multiple elements of a computer system in a single electronics package. For example, the single electronics package could contain the processor 710, the memory 720, the storage device 730, and input/output devices 740.

Although an example computer system has been described in FIG. 7, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the subject matter described herein. Other such embodiments are within the scope of the following claims.

What is claimed is:

1. A magnetic tracking system for determining an object pose of a tracked object in an environment of the magnetic tracking system, the magnetic tracking system comprising:
a scaffold;
a magnetic tracking device comprising:
a non-magnetic signal detector configured to measure a non-magnetic signal in the environment, wherein the non-magnetic signal is generated using a set of optical markers that are reconfigurable for placement at different locations within the environment; and
a magnetic signal detector configured to measure a magnetic signal in the environment, the magnetic signal detector being coupled to the non-magnetic signal detector, wherein the non-magnetic signal detector comprises a camera, and wherein the camera and the magnetic signal detector are movable to different portions of the scaffold within the environment to capture images of the optical markers at the different locations within the environment that are placed at known relative distances to one another based on a position of the scaffold;
a computing device configured to perform operations comprising:
receive a set of measurements of the non-magnetic signal and a corresponding measurement of the magnetic signal by moving the magnetic tracking device to a set of different locations in the environment at which one or more optical markers of the set of optical markers that are placed;
estimate, based on the set of measurements of the non-magnetic signal, a non-magnetic pose of the magnetic tracking device at the set of different locations in the environment,
estimate, based on the measurement of the magnetic signal, a magnetic pose of the magnetic tracking device in the environment for the set of different locations,
determine a difference between the magnetic pose estimate and the non-magnetic pose estimate for each location of the set of different locations;
determine a magnetic distortion correction value for each location of the set of different locations based on the difference at each of the different locations;
generate a distortion correction model including the magnetic distortion correction value for each of the different locations;
refine the distortion correction model by:
rearranging one or more sources of the non-magnetic signal in the environment;
receiving an updated a measurement of the non-magnetic signal based on the rearranged one or more sources of the non-magnetic signal; and
updating the distortion correction model using the updated measurement; and
output a representation of the distortion correction model.

2. The magnetic tracking system of claim 1, wherein the marker comprises an outer shape, the outer shape being distinct from other outer shapes of other markers of a plurality of markers in the environment.

3. The magnetic tracking system of claim 1, wherein the marker comprises an adhesive configured to removably affix the marker to another surface in the environment.

4. The magnetic tracking system of claim 1, wherein the marker comprises an infrared retroreflector, and wherein the non-magnetic signal detector comprises an infrared source.

5. The magnetic tracking system of claim 1, wherein the non-magnetic signal comprises one of an ArUco pattern, a ChArUco pattern, a light source, an ultrasonic source, a radio signal source, or an outer shape of a transmitter assembly.

6. The magnetic tracking system of claim 1, wherein the magnetic signal is generated by a transmitter assembly comprising:

a memory configured to store calibration data related to the transmitter assembly;

a processing device configured to control transmission of the magnetic signal from the transmitter assembly;

a communication interface for sending and receiving data from the computing device; and a power source configured to provide electrical power to the memory, the processing device, and the communication interface.

7. The magnetic tracking system of claim 1, wherein the operations further comprise:

tracking a tracked object by performing operations comprising:
receiving a measurement of the magnetic signal at a particular location in the environment;
retrieving the distortion correction model from a memory in communication with the computing device;
determining a particular pose estimate for the tracked object;
correcting the particular pose estimate based on a value of the distortion correction model corresponding to the particular location; and
outputting a representation of the corrected particular pose estimate.

8. The magnetic tracking system of claim 7, wherein the tracked object comprises one of a catheter, an endoscope, or a surgical instrument.

9. The magnetic tracking system of claim 1, wherein the operations further comprise:

receiving a plurality of measurements of the magnetic signal corresponding to a planar surface of the environment, the planar surface being associated with the scaffold that is positioned at a known location in the environment;

for each measurement of the plurality of measurements of the magnetic signal, retrieving a predetermined correction value associated with a location of the measurement in the environment;

determining, a distortion correction value for each measurement; and including the distortion correction value for each measurement in the distortion correction model.

* * * * *